(12) United States Patent
Evans et al.

(10) Patent No.: US 7,713,222 B2
(45) Date of Patent: May 11, 2010

(54) MEDICAL BANDAGING PRODUCT

(75) Inventors: John C. Evans, Nr Rochdale (GB);
Martin O'Hara, Charlotte, NC (US)

(73) Assignee: BSN Medical, Inc., Charlotte, NC (US)

( * ) Notice: Subject to any disclaimer, the term of this patent is extended or adjusted under 35 U.S.C. 154(b) by 528 days.

(21) Appl. No.: 10/595,353

(22) PCT Filed: Oct. 29, 2003

(86) PCT No.: PCT/US03/34239

§ 371 (c)(1),
(2), (4) Date: Apr. 13, 2007

(87) PCT Pub. No.: WO2005/051249

PCT Pub. Date: Jun. 9, 2005

(65) Prior Publication Data

US 2007/0276302 A1 Nov. 29, 2007

(51) Int. Cl.
*A61F 5/00* (2006.01)
*A61F 13/00* (2006.01)
(52) U.S. Cl. .................... 602/8; 602/5; 602/6; 602/44; 602/63; 602/76

(58) Field of Classification Search ................ 602/41, 602/42, 3, 44, 63, 76, 5–8
See application file for complete search history.

(56) References Cited

U.S. PATENT DOCUMENTS

| 4,621,624 | A | | 11/1986 | Rayboy |
| 5,526,656 | A | * | 6/1996 | Conroy, Jr. et al. ............ 66/193 |
| 5,531,667 | A | | 7/1996 | Webb et al. |
| 5,807,291 | A | | 9/1998 | Larson et al. |
| 5,807,295 | A | | 9/1998 | Hutcheon et al. |
| 6,186,966 | B1 | | 2/2001 | Grim et al. |
| 2004/0016444 | A1 | * | 1/2004 | Mitchell, Jr. et al. ........... 134/6 |
| 2004/0024338 | A1 | * | 2/2004 | Evans ............................. 602/8 |
| 2005/0267392 | A1 | * | 12/2005 | Evans ......................... 602/42 |
| 2006/0009721 | A1 | * | 1/2006 | Evans ............................. 602/5 |
| 2007/0043312 | A1 | * | 2/2007 | Lee ................................. 602/6 |

\* cited by examiner

*Primary Examiner*—Kim M Lewis
(74) *Attorney, Agent, or Firm*—Adams Intellectual Property Law

(57) ABSTRACT

A medical bandaging product fabricated of a rib-knitted fabric constructed of synthetic yarns selected from the group of acrylic, polyester and polypropylene yarns. An elastic yarn provides elasticity to the fabric, and an effective amount of a water repelling treatment is applied to the fabric for imparting water-repellent characteristics. The fabric may be used as a cast liner or as a protective wrapping of a splint product.

13 Claims, 20 Drawing Sheets

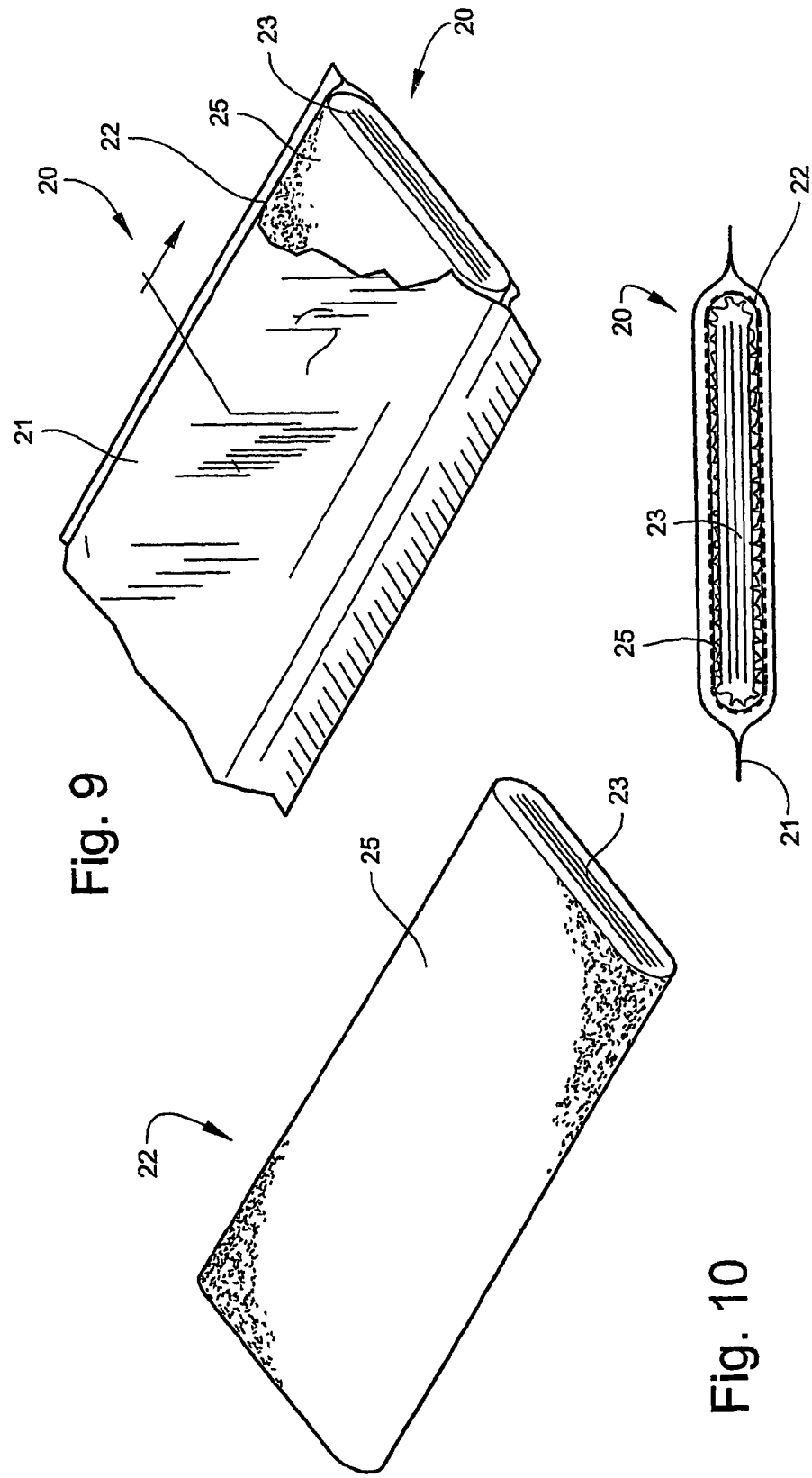

MEDICAL BANDAGING PRODUCT

TECHNICAL FIELD AND BACKGROUND OF THE INVENTION

This invention relates to a water-resistant medical bandaging product according to several alternative embodiments. The medical bandaging product has application as a cast liner and as a cushion layer, for example, of a splint product. In either case, the medical bandaging product may be fabricated for use in pre-cut or continuous length form.

In the cast liner application the cast liner serves to protect the skin of a patent from the rigid or semi-rigid surface of a cast tape or other rigid material by which the limb is being immobilized during healing. The water-resistant nature of the bandage substantially reduces moisture retention both from patient perspiration and from wetting from the outside, such as when bathing. This, in turn, provides a more comfortable, long-lasting bandage that resists odor and itching. The knit construction of the bandage provides conformability to the patient anatomy, particularly in joint areas, such as elbow, ankle and foot where acute angles can create creases in the bandage causing pressure points.

SUMMARY OF THE INVENTION

Therefore, it is an object of the invention to provide a bandage that is water-resistant.

It is another object of the invention to provide a bandage that is soft and durable.

It is another object of the invention to provide a tubular bandage that is capable of being formed by a tubular or flat knitting process.

It is another object of the invention to provide a bandage that can be packaged in either pre-cut or continuous lengths.

It is another object of the invention to provide a bandage that has a water-resistant coating formed from an applied silicone or polyurethane-based monomer.

It is another object of the invention to provide a bandage that has a radial knit construction that provides fold regions in order to reduce or eliminate creasing of the bandage when the bandage is applied under a cast.

It is another object of the invention to provide a bandage that is fabricated as a cast liner for being positioned on a limb between the skin and a rigid or semi-rigid cast material.

It is another object of the invention to provide a bandage that is fabricated as a splint cushion positioned over a supporting substrate.

These and other objects of the present invention are achieved in the preferred embodiments disclosed below by providing a medical bandaging product, comprising a rib-knitted fabric constructed of synthetic yarns selected from the group consisting of acrylic, polyester and polypropylene yarns, and an effective amount of a water-repelling treatment applied to the fabric for imparting water-repellent characteristics to the fabric.

According to one preferred embodiment of the invention, said db-knitted fabric is circular-knitted to define a tube, with ribs extending longitudinally along the length of the tube.

According to another preferred embodiment of the invention, said rib-knitted fabric is circular-knitted to define a tube, with ribs extending radially around the periphery of the tube.

According to yet another preferred embodiment of the invention, the medical bandaging product includes an elastic yarn incorporated into the fabric to provide elasticity to the fabric.

According to yet another preferred embodiment of the invention, said medical bandaging product comprises a cast liner for being positioned over a limb to be treated and under a cast material.

According to yet another preferred embodiment of the invention, a splint product is provided in roll form for being dispensed in predetermined lengths suitable for a given medical use, and comprises an elongate sleeve formed of moisture-impervious material and sealable to prevent entry of moisture. An elongate medical material is positioned in said sleeve and sealed therein against entry of moisture until use. The medical material comprises a substrate, a reactive system impregnated into or coated onto said substrate, said system remaining stable when maintained in substantially moisture-free conditions and hardening upon exposure to sufficient moisture to form a rigid, self supporting structure, and a soft, flexible, protective tubular wrapping enclosing said substrate along its length to provide a cushioning barrier between the substrate and the skin of a patient when the material is in use, said soft, flexible protective wrapping comprising a rib-knitted fabric constructed of synthetic yarns selected from the group consisting of acrylic, polyester and polypropylene yarns. Means are provided for resealing said sleeve against entry of moisture after a predetermined length of said bandaging product has been dispensed for use to prevent hardening of said substrate remaining in said sleeve.

According to yet another preferred embodiment of the invention, said rib-knitted fabric of the protective wrapping is circular-knitted to define a tube, with ribs extending longitudinally along the length of the tube.

According to yet another preferred embodiment of the invention, said rib-knitted fabric of the protective wrapping is circular-knitted to define a tube, with ribs extending radially around the periphery of the tube.

According to yet another preferred embodiment of the invention, the protective wrapping includes an elastic yarn incorporated into the fabric to provide elasticity to the fabric.

According to yet another preferred embodiment of the invention, the protective wrapping comprises a knitted fabric constructed of synthetic yarns selected from the group consisting of acrylic, polyester and polypropylene yarns, said fabric having a knit structure wherein a major surface of the fabric comprises regular courses and wales of soft, deformable tufts defined by yarn loops extending outwardly above a base of the fabric.

According to yet another preferred embodiment of the invention, a splint product in roll form is provided for being dispensed in predetermined lengths suitable for a given medical use, comprising an elongate sleeve formed of moisture-impervious material and sealable to prevent entry of moisture and an elongate medical material positioned in said sleeve and sealed therein against entry of moisture until use. The medical material comprises a substrate, a reactive system impregnated into or coated onto said substrate, said system remaining stable when maintained in substantially moisture-free conditions and hardening upon exposure to sufficient moisture to form a rigid, self supporting structure. A medical bandaging product comprising a soft, flexible protective wrapping enclosing said substrate along its length to provide a cushioning barrier between the substrate and the skin of a patient when the material is in use. The protective wrapping comprises a rib-knitted fabric constructed of synthetic yarns selected from the group consisting of acrylic, polyester and polypropylene yarns. Means are provided for resealing said sleeve against entry of moisture after a predetermined length of said bandaging product has been dispensed for use to prevent hardening of said substrate remaining in said sleeve.

According to yet another preferred embodiment of the invention, a cast liner is provided comprising a rib-knitted fabric constructed of synthetic yarns selected from the group consisting of acrylic, polyester and polypropylene yarns, and an effective amount of a water-repelling treatment applied to the fabric for imparting water-repellent characteristics to the fabric.

BRIEF DESCRIPTION OF THE DRAWINGS

Some of the objects of the invention have been set forth above. Other objects and advantages of the invention will appear as the invention proceeds when taken in conjunction with the following drawings, in which:

FIG. 9 is a partial perspective view with parts broken away of a synthetic splint product utilizing the medical bandaging product as a protective cushion between the patient and the substrate;

FIG. 10 is a perspective view of a cut length of the synthetic splint product removed from the foil protective sleeve;

FIG. 11 is a cross-section of the synthetic splint product shown in FIG. 10;

DESCRIPTION OF THE PREFERRED EMBODIMENT AND BEST MODE

Figure 1:
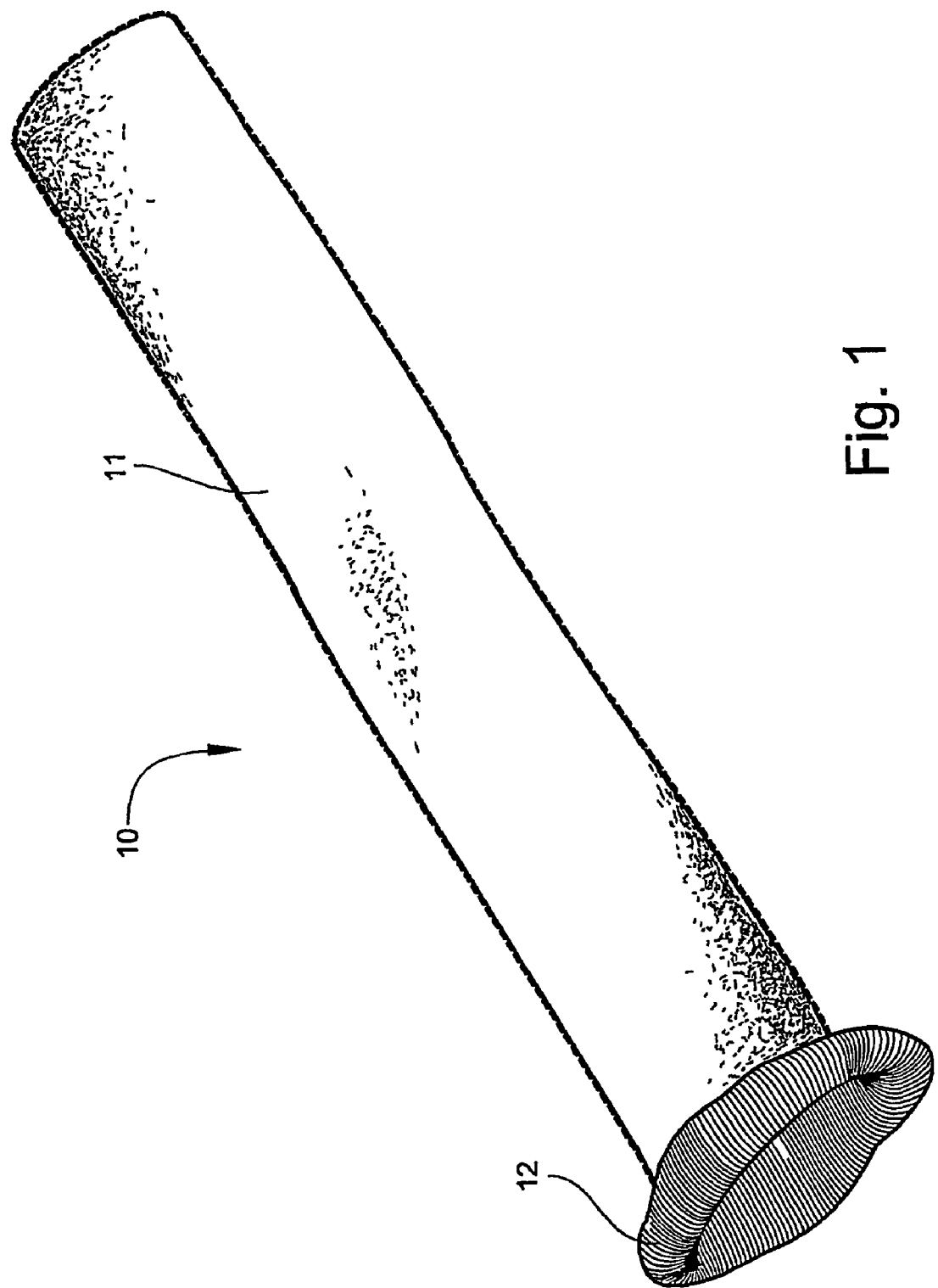
FIG. 1 is a perspective view of a medical bandaging product in the form of a cast liner according to one embodiment of the invention.
Figure 2:
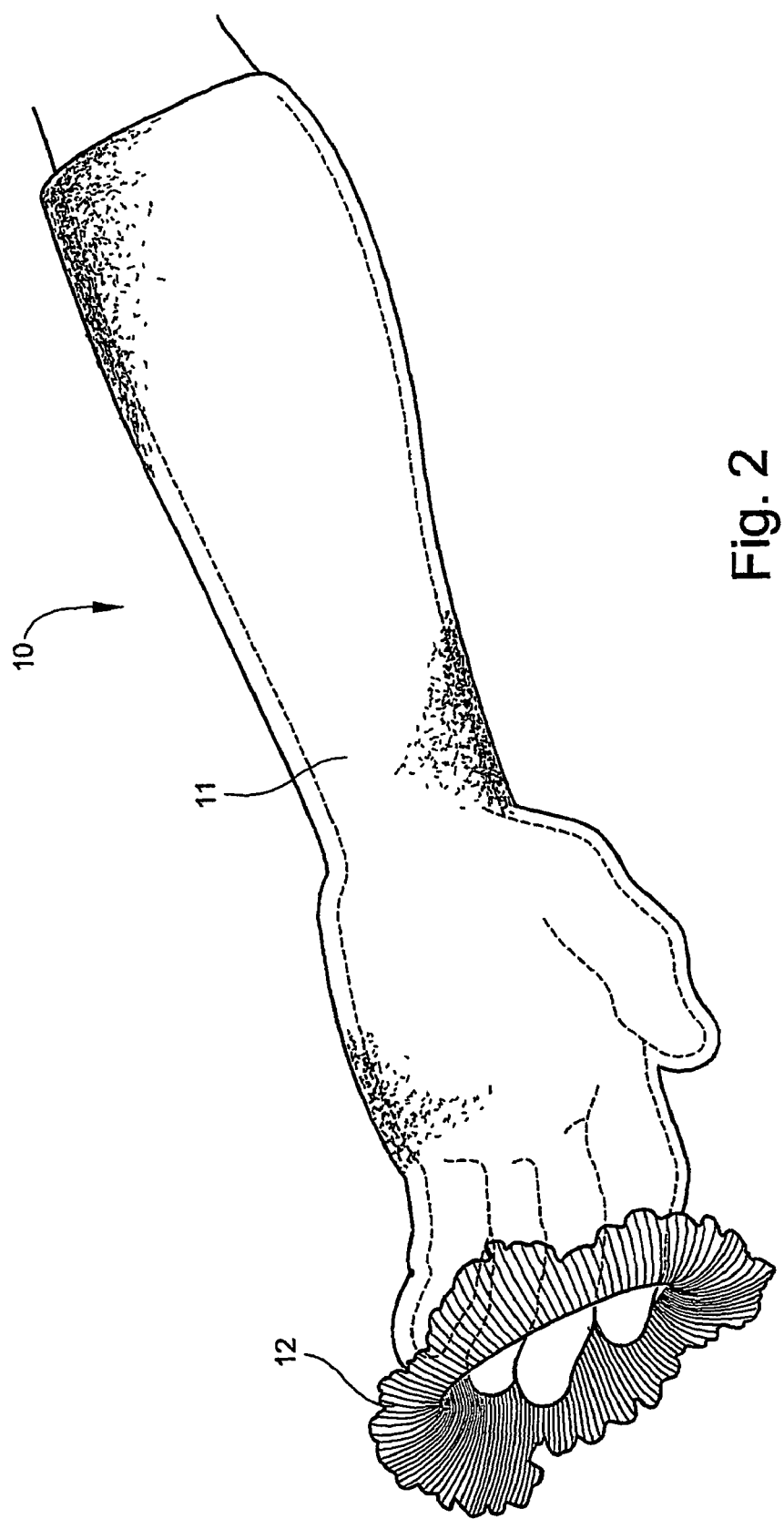
FIGS. 2-6 are views showing a length of the cast liner being applied to the forearm of a patient and formed into a cast with an overlying cast tape.
Figure 3:
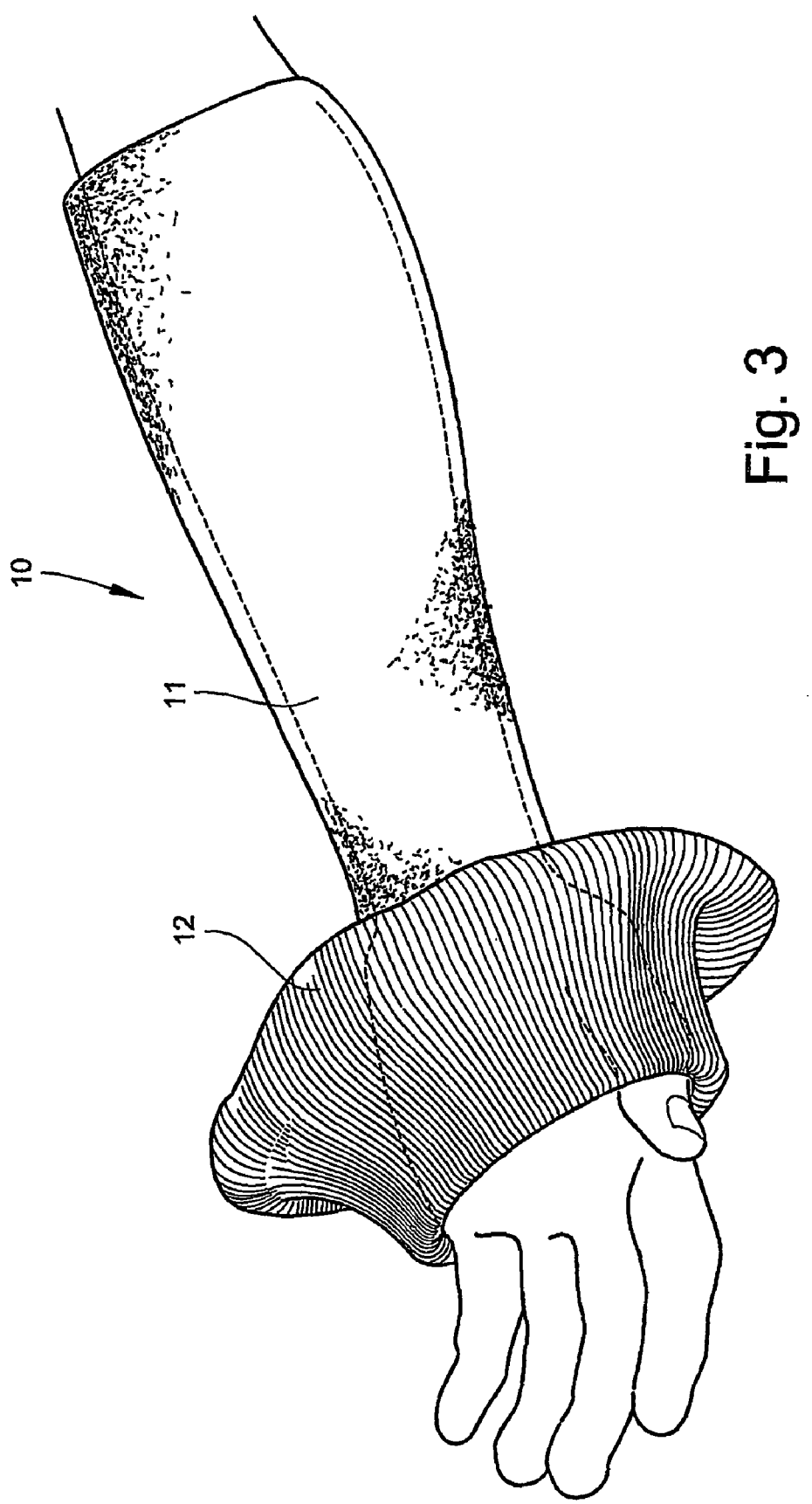
Figure 4:
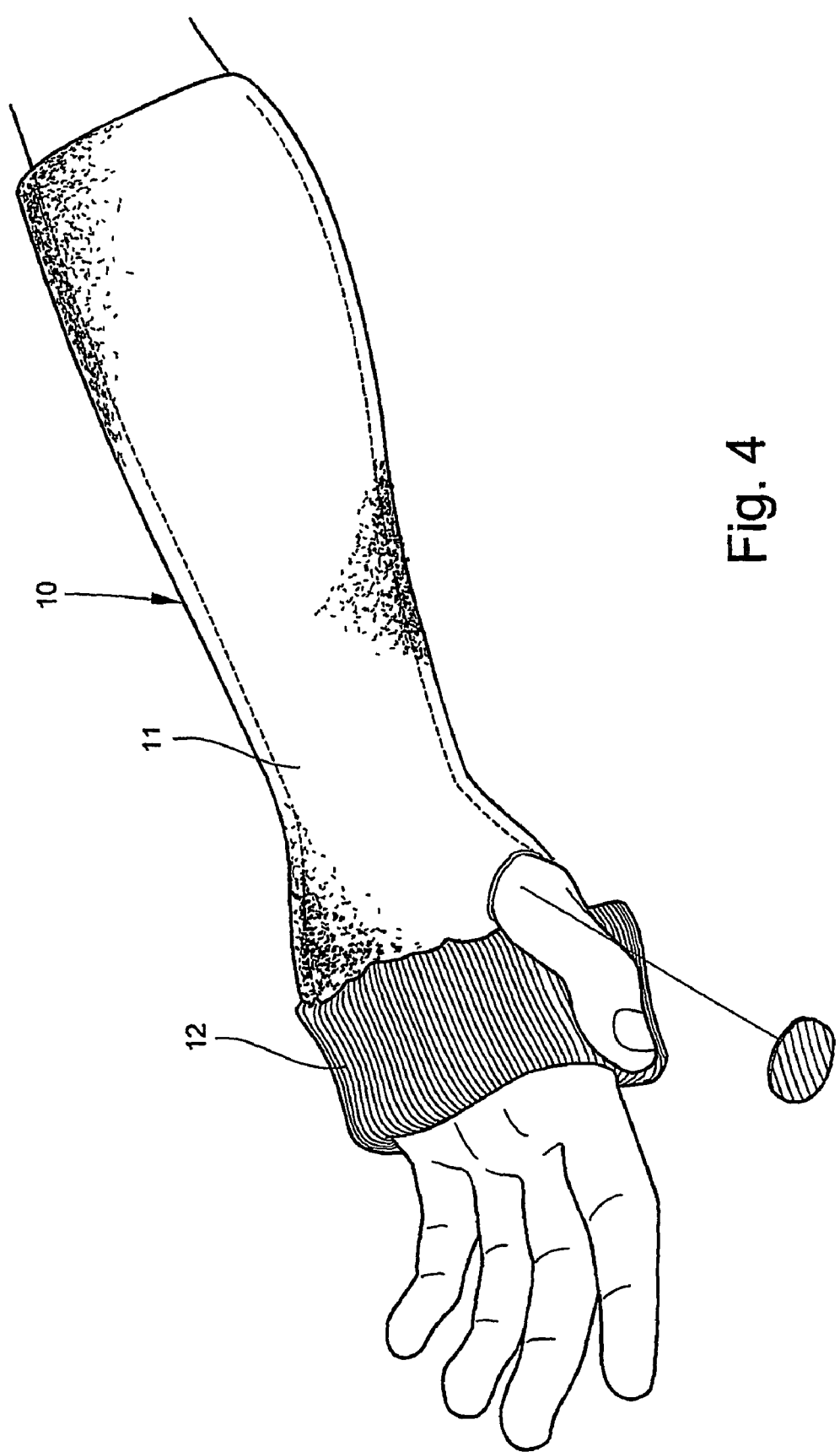
Figure 5:
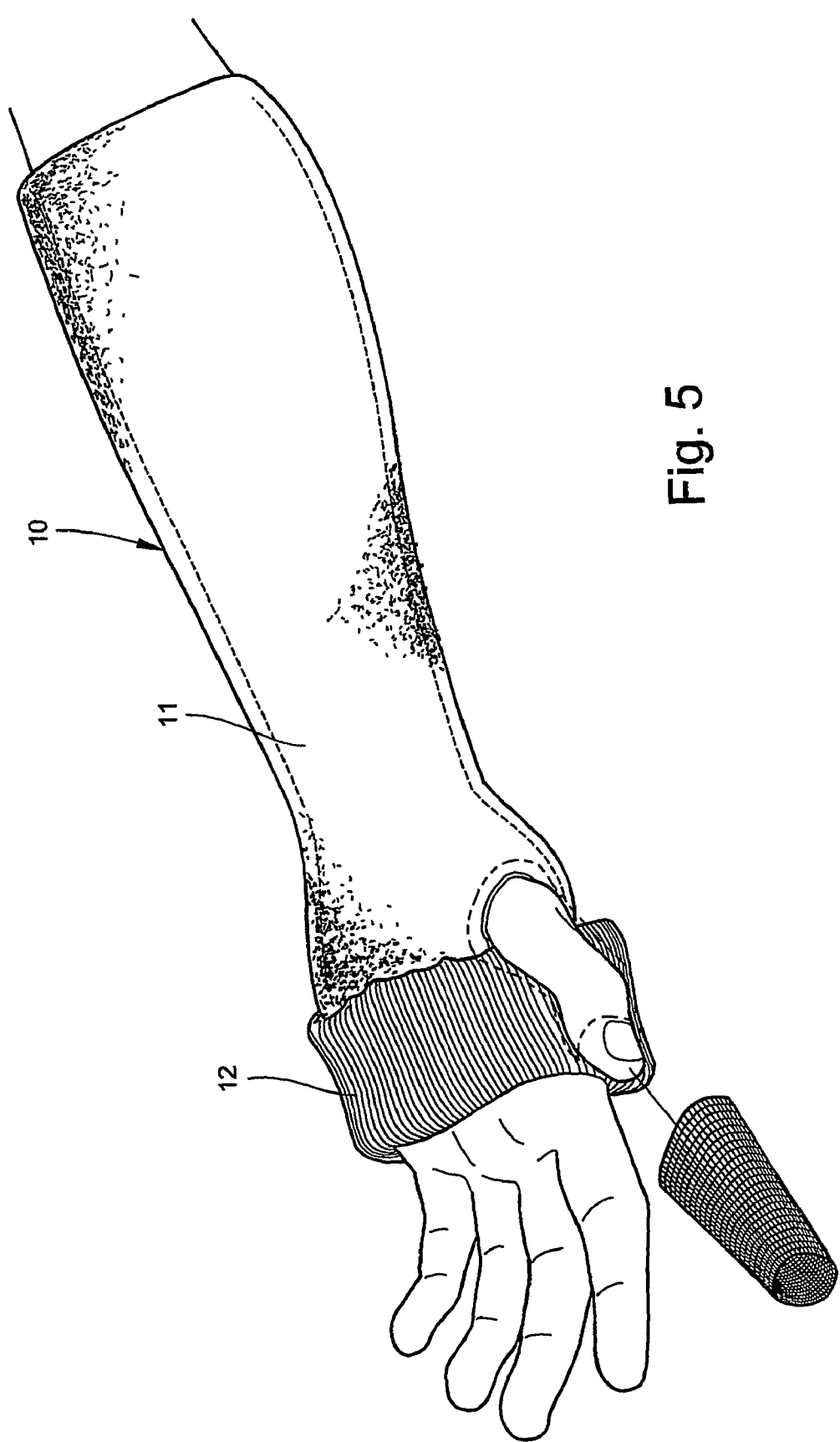
Figure 6:
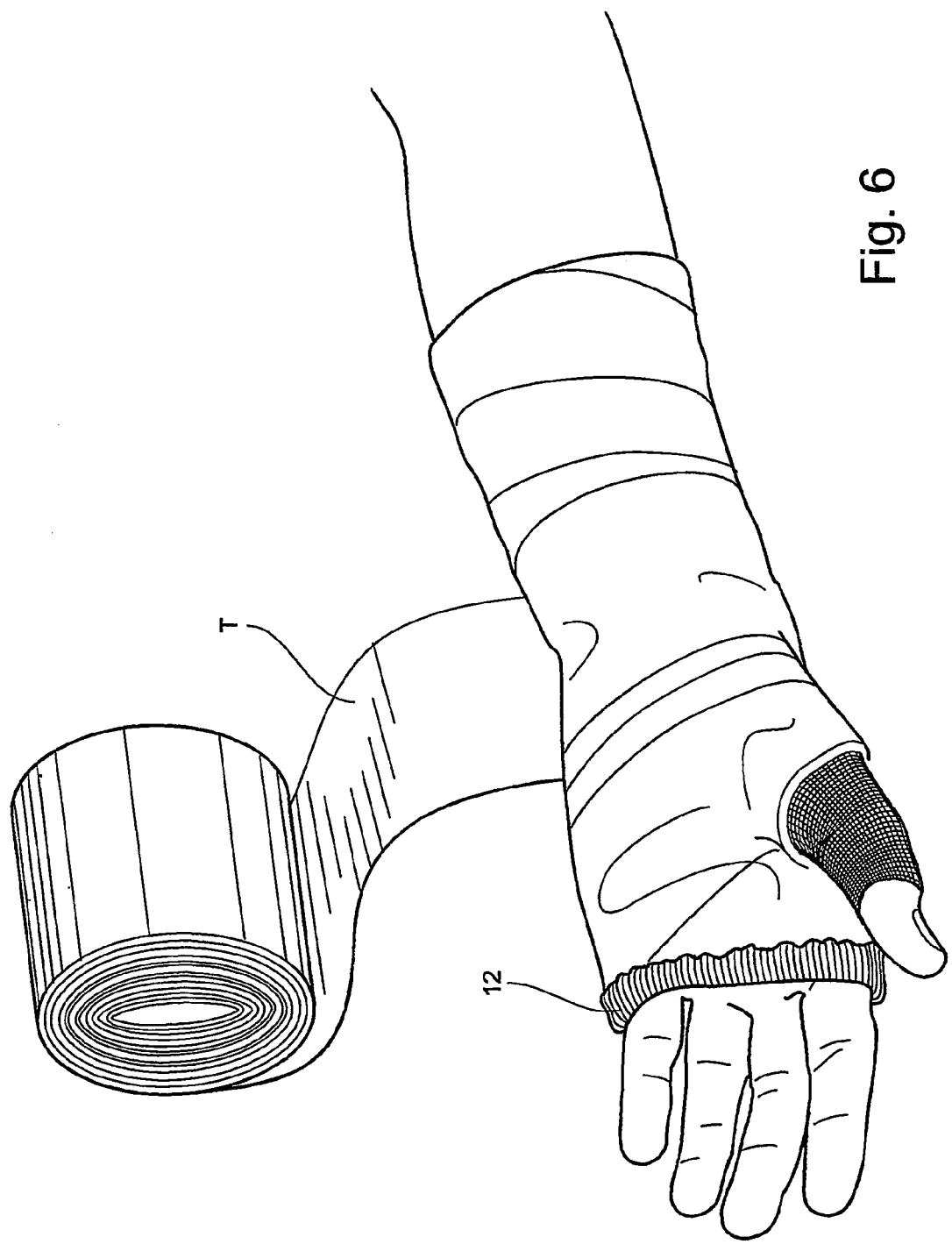

Referring now specifically to the drawings, a cast liner according to one embodiment of the present invention is illustrated in FIG. 1 and shown generally at reference numeral 10. The cast liner 10 is shown, as intended for use, in tubular form. The tube may be formed by knitting a yarn or a sliver on a conventional circular knitting machine, or knitting on a flat-bed machine, and then forming the flat fabric into a tube using a seam, such as an overedge or serging seam. The knitting machine may have a double-knit capability.

The cast liner 10 is knitted from spun synthetic fiber yarns, such as conventional or microfiber acrylic, polypropylene or polyester yarns. The water-resistant nature of the cast liner 10 results from a process of coating the knitted fabric with a silicone or polyurethane-based monomer. The cast liner 10 may be formed from filament or spun yarns, with spun textured yarns being the preferred construction. An elastic yarn provides stretch and recovery to the cast liner 10.

In general, the outer surface 11 of the cast liner 10 has a soft, plush appearance and feel resulting from the use of synthetic slivers or yarns having a Dtex range of between 10 s to a 4 cotton. The inner surface 12 shows a distinct rib appearance with the ribs running longitudinally along the length of the cast liner 10.

The preferred construction is a double jersey 2 in 1 rib with the ribs spaced between ⅛" and 1/16" apart. The cast liner 10 may be formed into tubes have diameters of between 1" and 6", with a diametrical expansion of between 20-60 percent. This permits use of the cast liner 10 on a wide variety of patient sizes with a degree of expansion that permits a snug, conforming fit without reducing circulation in the affected area. Elongation along the longitudinal axis is preferably between 20 and 30 percent. A variety of other knit patterns is also possible, so long as the essential characteristics of the cast liner 10 remain the same.

The approximate weight is between 150-250 grams for a cast liner 10 having a thickness of between 0.01 and 0.018".

The add-on of the water-resistant coating is between 30-80 percent by weight.

Alternatively, a waterproofing agent comprised of water, organic alcohol and complex fatty waxes, such as Eco 2000 waterproofing manufactured by Eco2000 Pty Ltd, Mornington, Australia may be suitable for some applications at an application rate of between 5-10 square meters of fabric per liter of waterproofing. This agent penetrates rather than coats the fibers of the cast liner.

Referring now to FIGS. 2-6, the cast liner 10 is shown being applied to a limb and wrapped with a conventional cast tape "T". The cast liner 10 is applied with the ribbed inner surface 12 next to the skin. The ribs, which separate slightly when applied to the limb, provide enhanced air flow and moisture removal from the skin.

Figure 7:
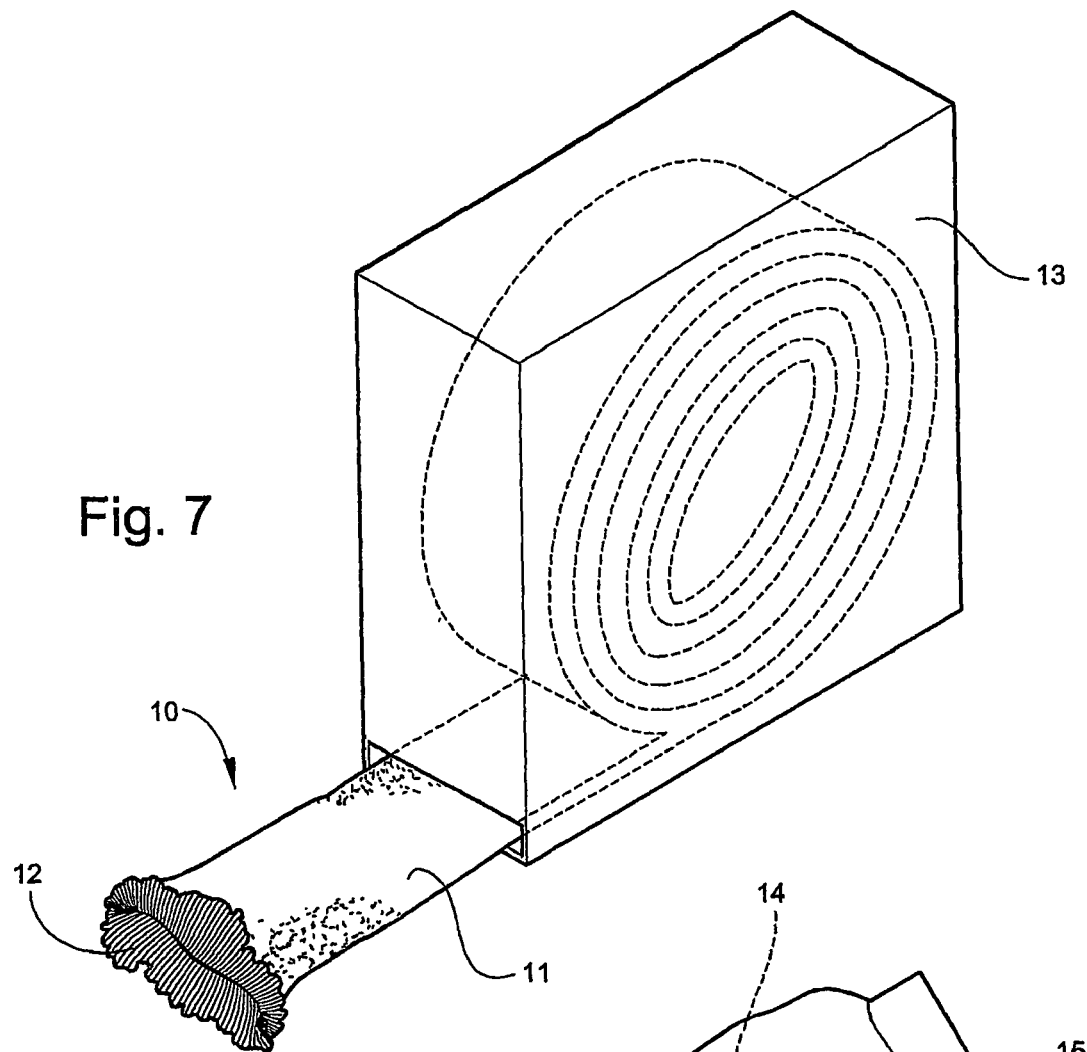
FIG. 7 shows a continuous length of the cast liner in a dispensing package.

Referring to FIG. 7, a continuous length, for example 10-15 meters, of the cast liner 10 is shown formed into a coil and packaged in a dispensing box 13. A desired length is obtained by extracting the free end of the cast liner 10 from the dispensing box 13 and cutting off the desired length.

Figure 8:
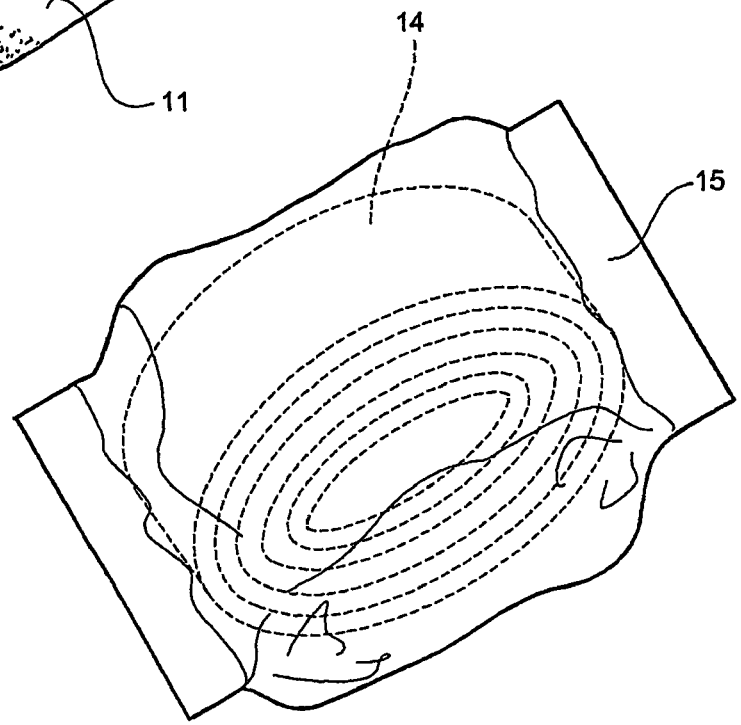
FIG. 8 shows a pre-cut length of the cast liner packaged for distribution and storage until ready for use.

A pre-cut length 14 of the cast liner 10 is shown in FIG. 8, packaged in rolled form in a protective package 15. The pre-cut length 14 of the cast liner is formed by cutting a longer length of the cast liner 10 into the desired lengths, and then packaging them in a suitable fashion for subsequent use.

Referring now to FIGS. 10-13, the same medical bandaging product used as the cast liner 10 can be used as a padding layer for a medical bandaging product of the type that incorporates a moisture curable resin into a substrate for use as a splint.

The medical bandaging product 20 is comprised generally of an outer elongate tubular sleeve 21 which is formed of a moisture-impervious material such as a laminated plastic/aluminum film heat sealed along opposite, parallel extending sides.

An elongate splint material 22, described in detail below, is positioned within sleeve 21 and is maintained in substantially moisture-free conditions until dispensed. The end of sleeve 21 is sealed with sealing means, such as a clamp, to prevent hardening of the unused portion of the splint material 22.

Once the appropriate length of the splint material 22 has been dispensed and cut from the roll, it is removed from sleeve 21 and the cut portion of the sleeve 21 is discarded.

Splint material 22 comprises a substrate 23 comprised of a suitable number of overlaid layers, for example, 6 layers, of a woven or knitted relatively open fabric, constructed of, for example, fiberglass, or various combinations of synthetic fibers. Substrate 23 is contained within a tubular length of a padding layer 25 having a construction as identified above with relation to the cast liner 10. The padding layer 25 provides a cushioning protective layer between the skin of the patient and substrate 23. Substrate 23 is impregnated or coated with a reactive system which remains stable when maintained in substantially moisture-free conditions but which hardens upon exposure to sufficient moisture to form a rigid, self-supporting structure. A typical formulation of the reaction system is set forth in the following table:

| Typical Formulation: | | |
|---|---|---|
| Isonate↓ 143L or Mondur↓ CD or Rubinate ↓ XI168 | polyisocyanate | 50.0% |
| Pluracol↓ P1010 | polyol | 46.6% |
| DC-200 Silicone | defoaming agent | 0.30% |
| Benzoyl Chloride | stabilizer | 0.10% |
| Thancat↓ DM-70 | catalyst | 3.0% |
| | | 100% |

A complete discussion of the parameters of the reactive system, the manner of production and the variables which apply are found in U.S. Pat. No. 4,411,262, referred to above.

Hardening of the substrate 23 and thus of the splint material 22 is activated by dipping or spraying with water. Then excess moisture is squeezed from the splint material 22 with a towel.

Figure 12:
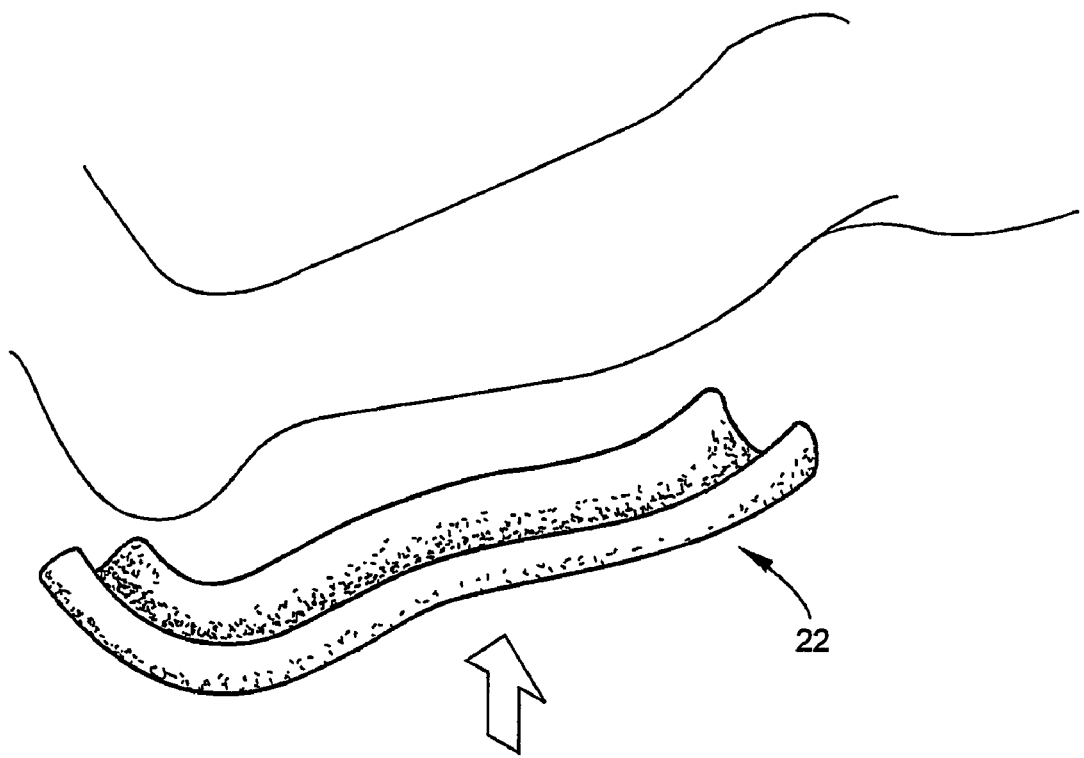
FIGS. 12 and 13 show application of a length of the synthetic splint product to a limb.
Figure 13:
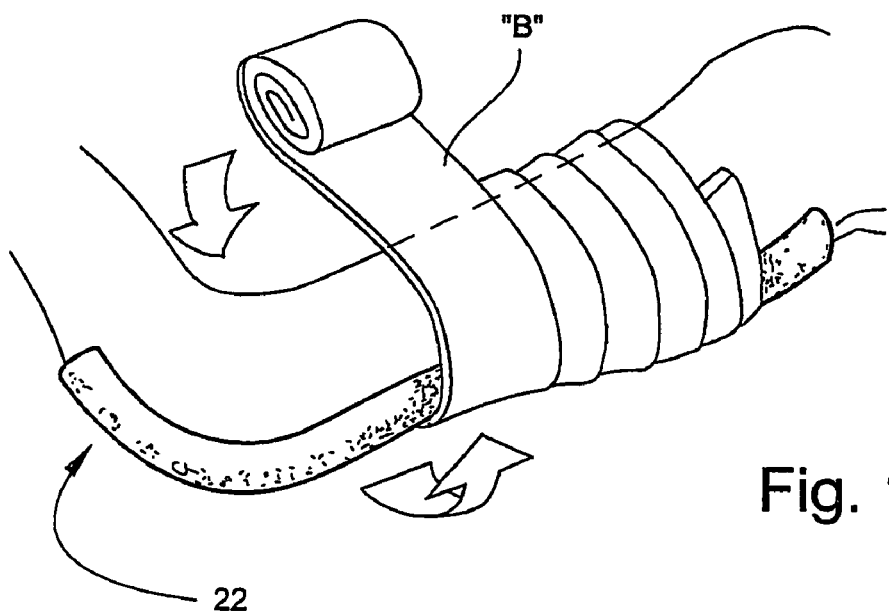

Referring now to FIG. 12, an appropriate length of splint material 22 is formed to the shape of the body member to be immobilized. This particular type of splint, known as a posterior short leg splint, is formed by molding a length of the splint material 22 to the calf and up over the heel and onto the foot. Then, splint material 22 is overwrapped with a conventional elastic bandage "B", as is shown in FIG. 13.

Figures 14, 15:
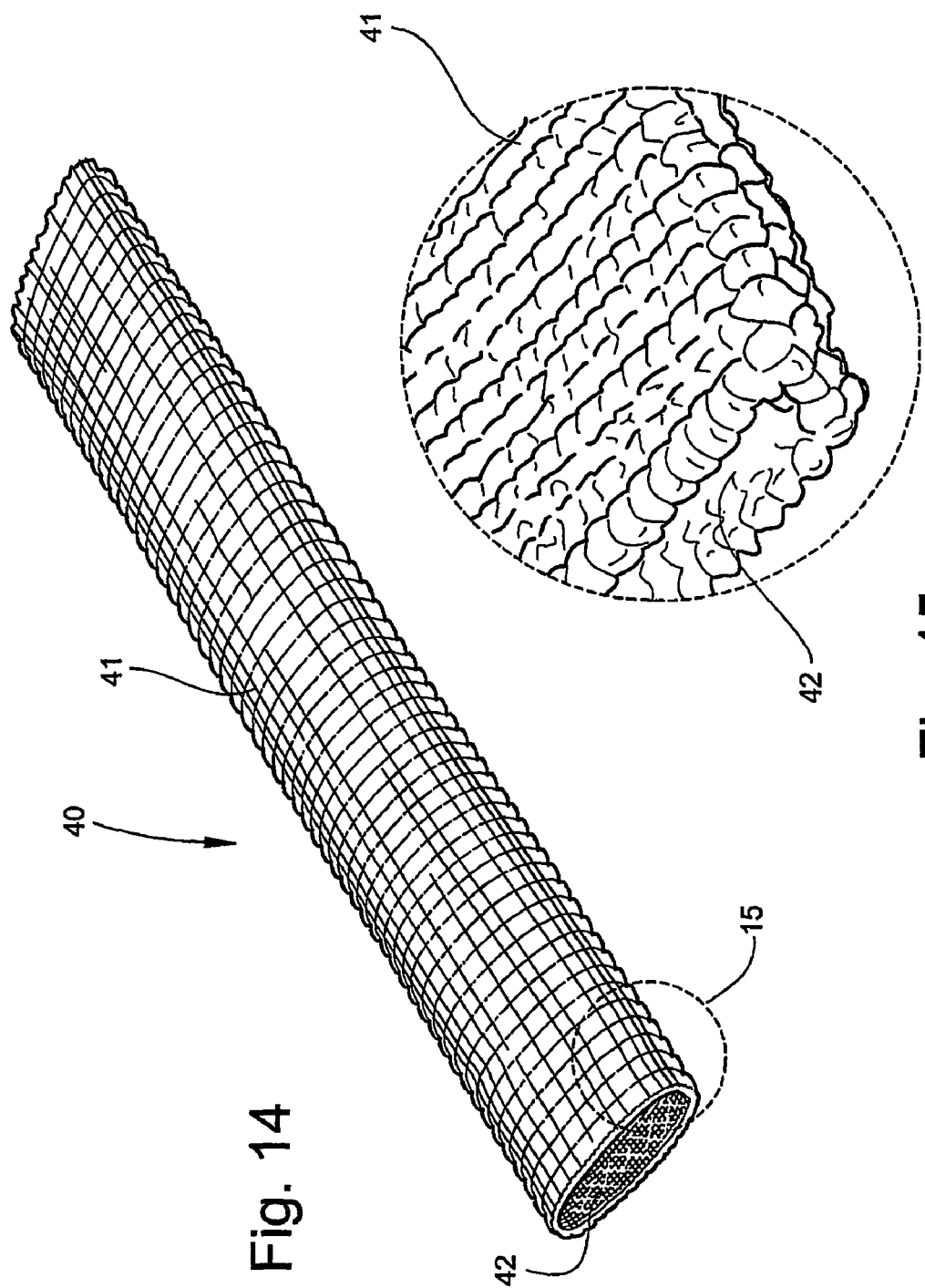
FIG. 14 is a perspective view of a length of a medical bandaging product according to an alternative embodiment of the invention having a "popcorn" surface texture.
FIG. 15 is an enlarged view of the textured outer surface of the medical bandaging product shown in FIG. 14.
Figure 16:
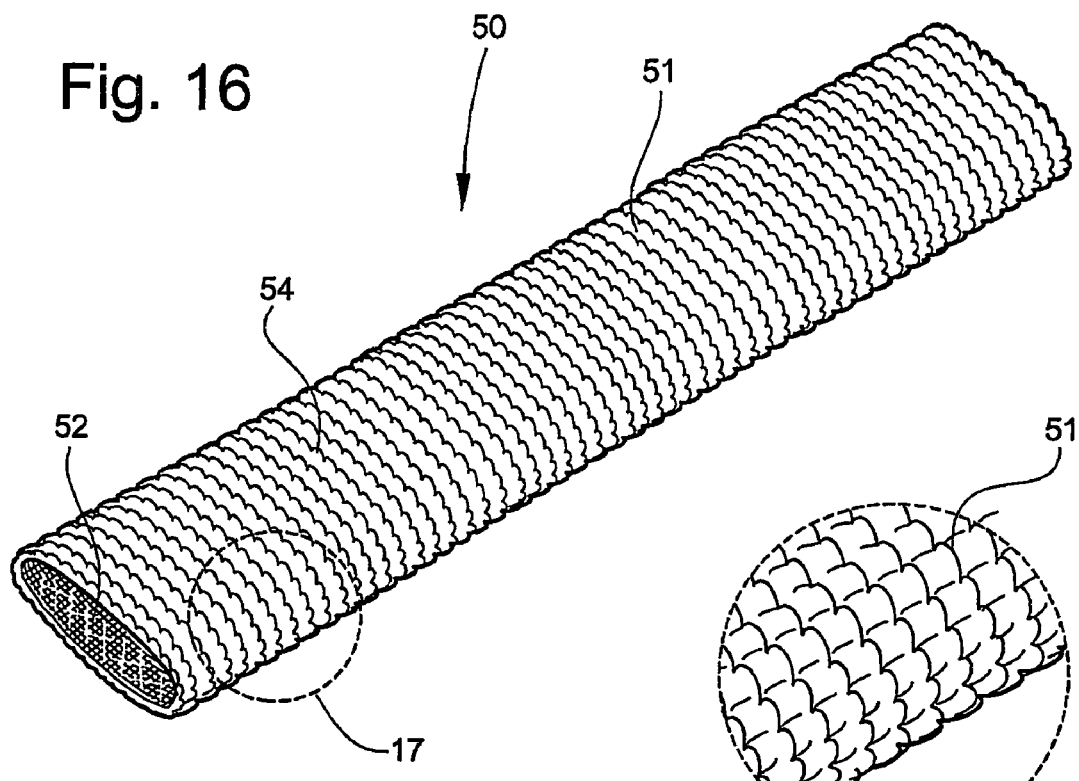
FIG. 16 is a perspective view of a length of medical material according to an alternative embodiment of the invention.
Figure 17:
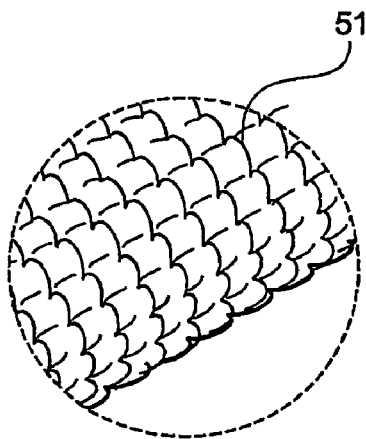
FIG. 17 is an enlarged view of the outer surface of the medical bandaging product.
Figure 18:
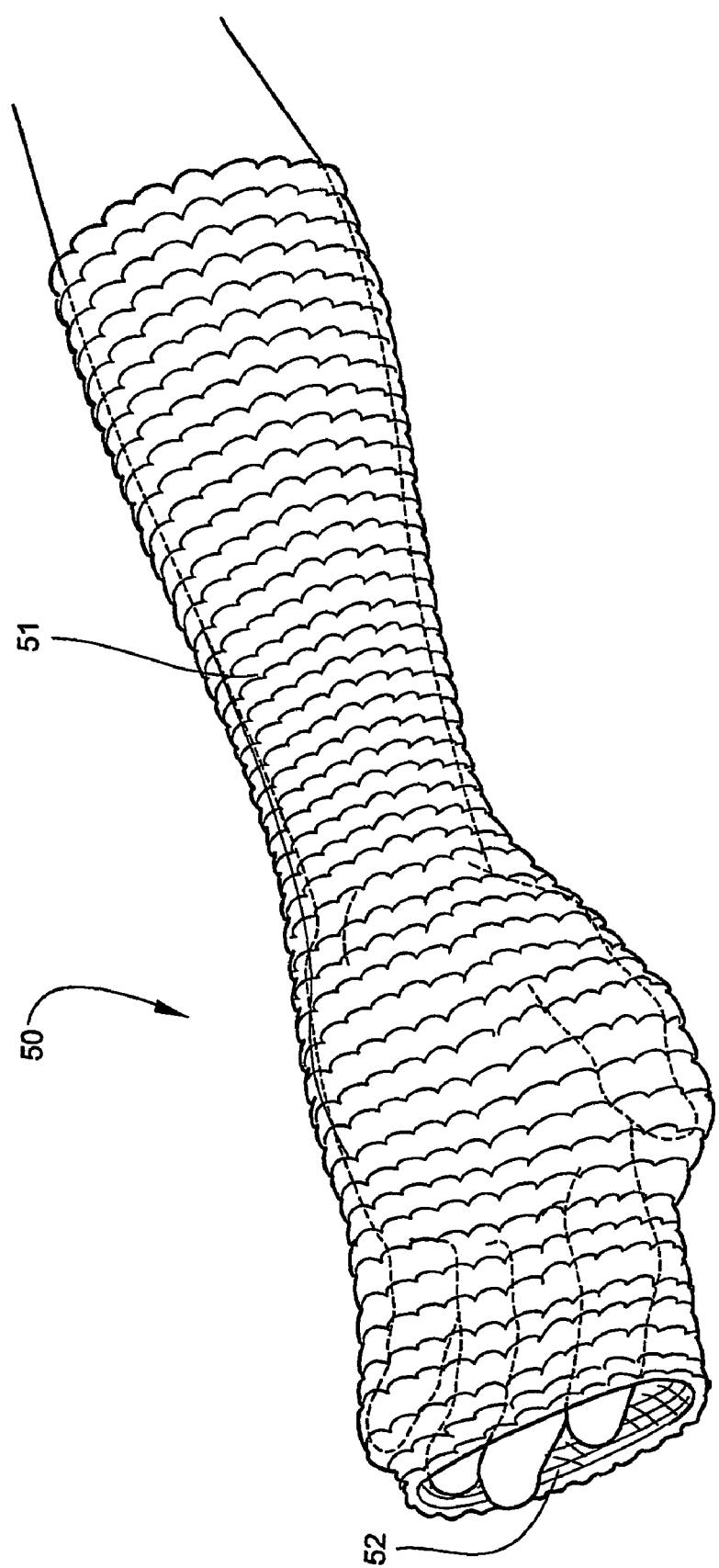
FIGS. 18-22 are views showing a length of the medical bandaging product being applied as a cast liner to the forearm of a patient and formed into a cast with an overlying cast tape.
Figure 19:
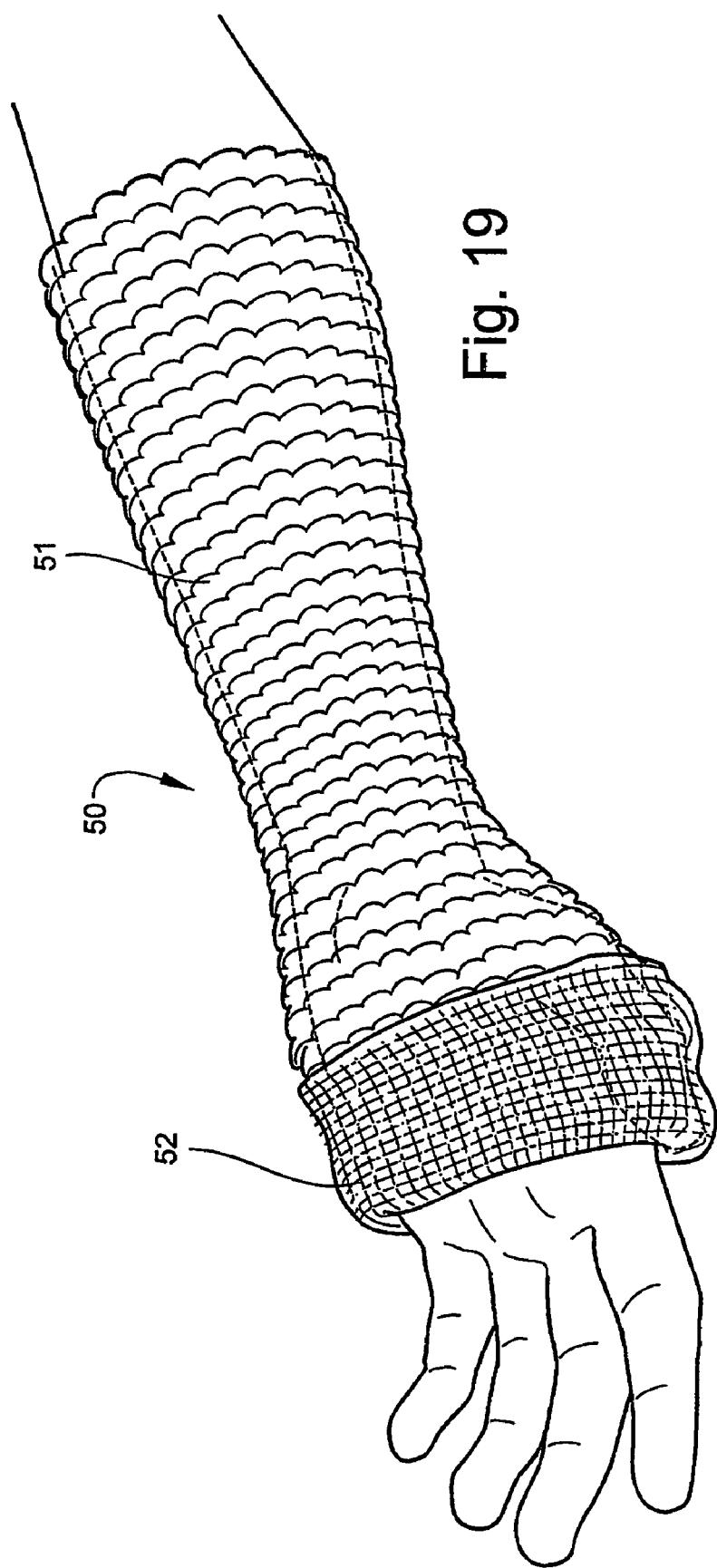
Figure 20:
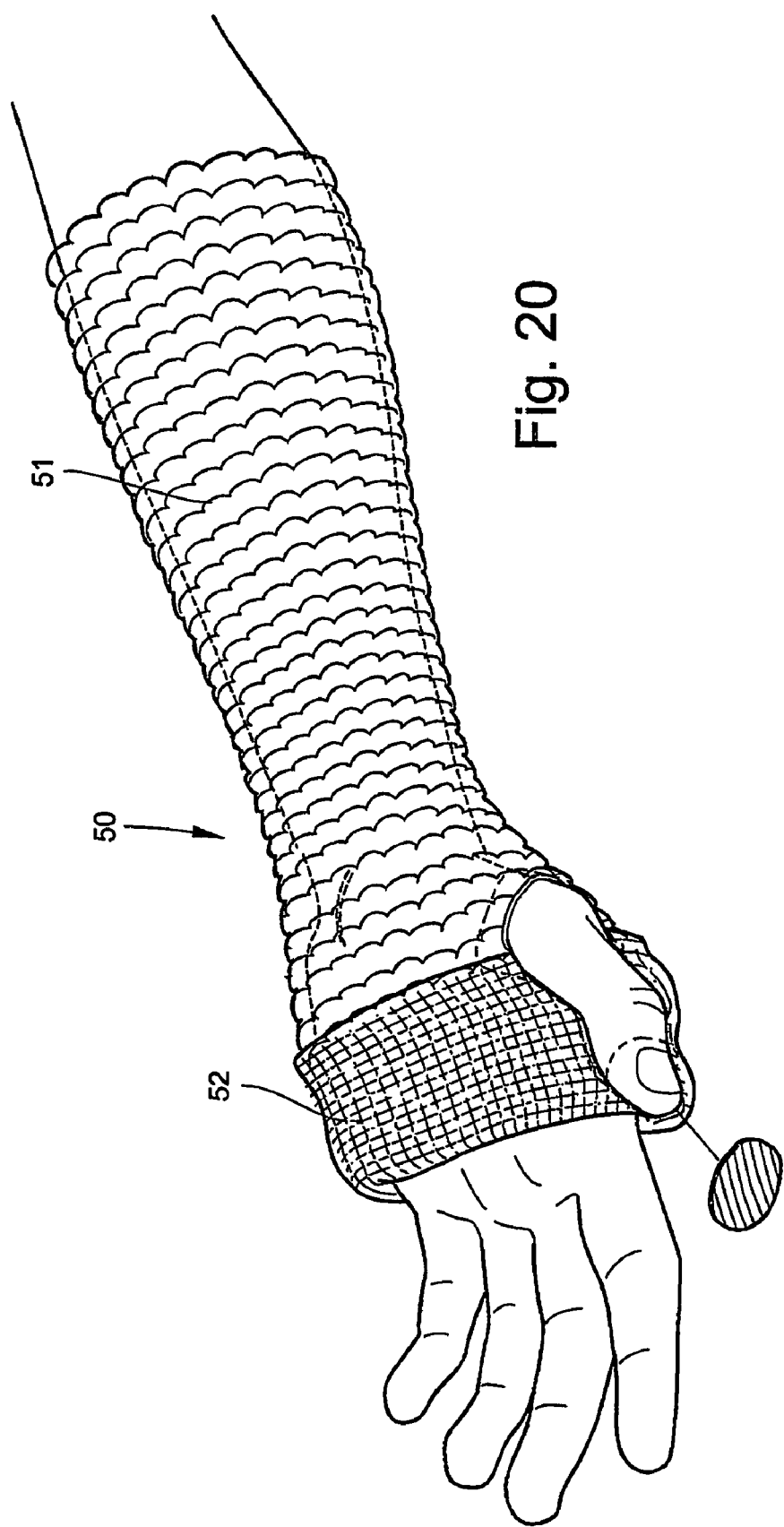
Figure 21:
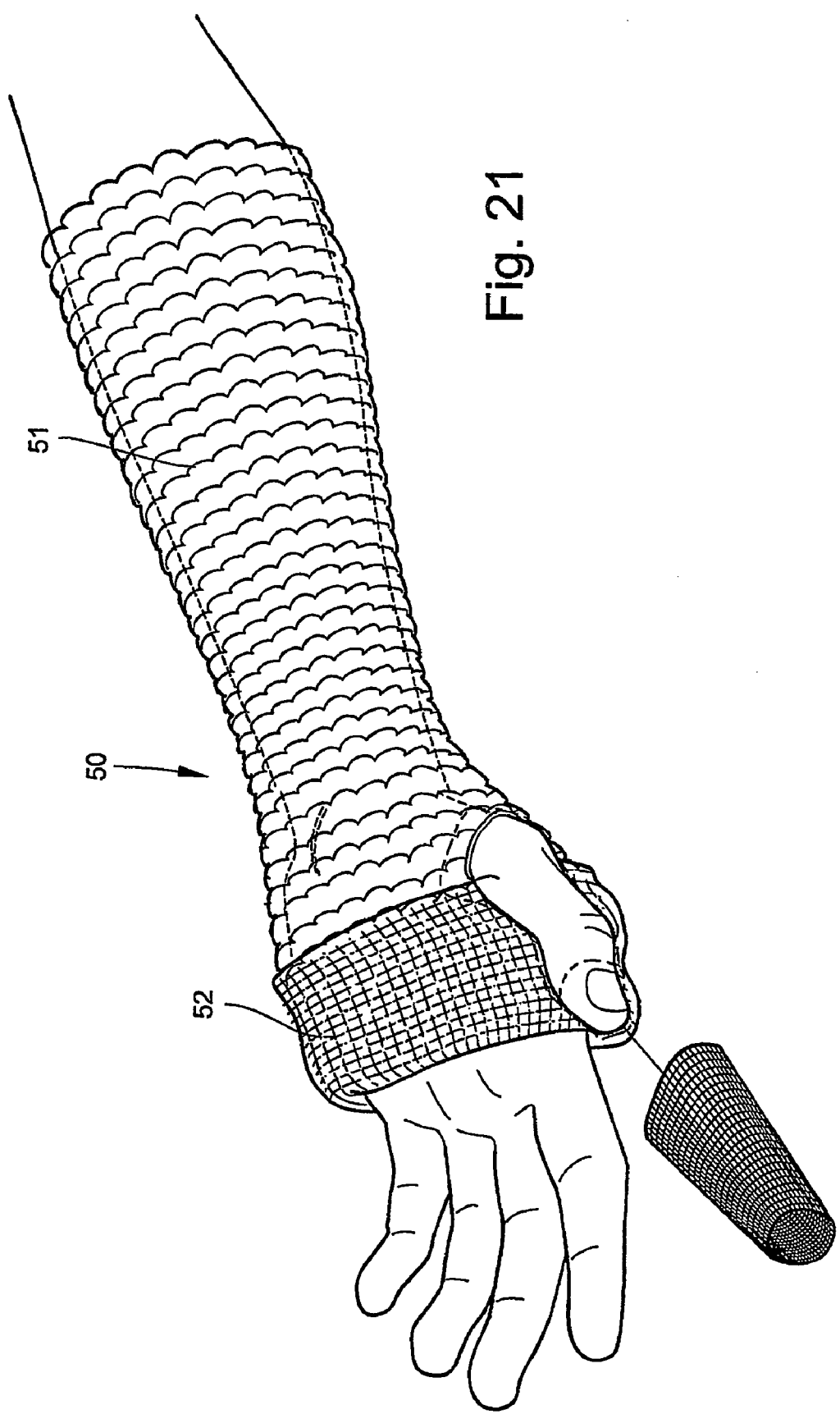
Figure 22:
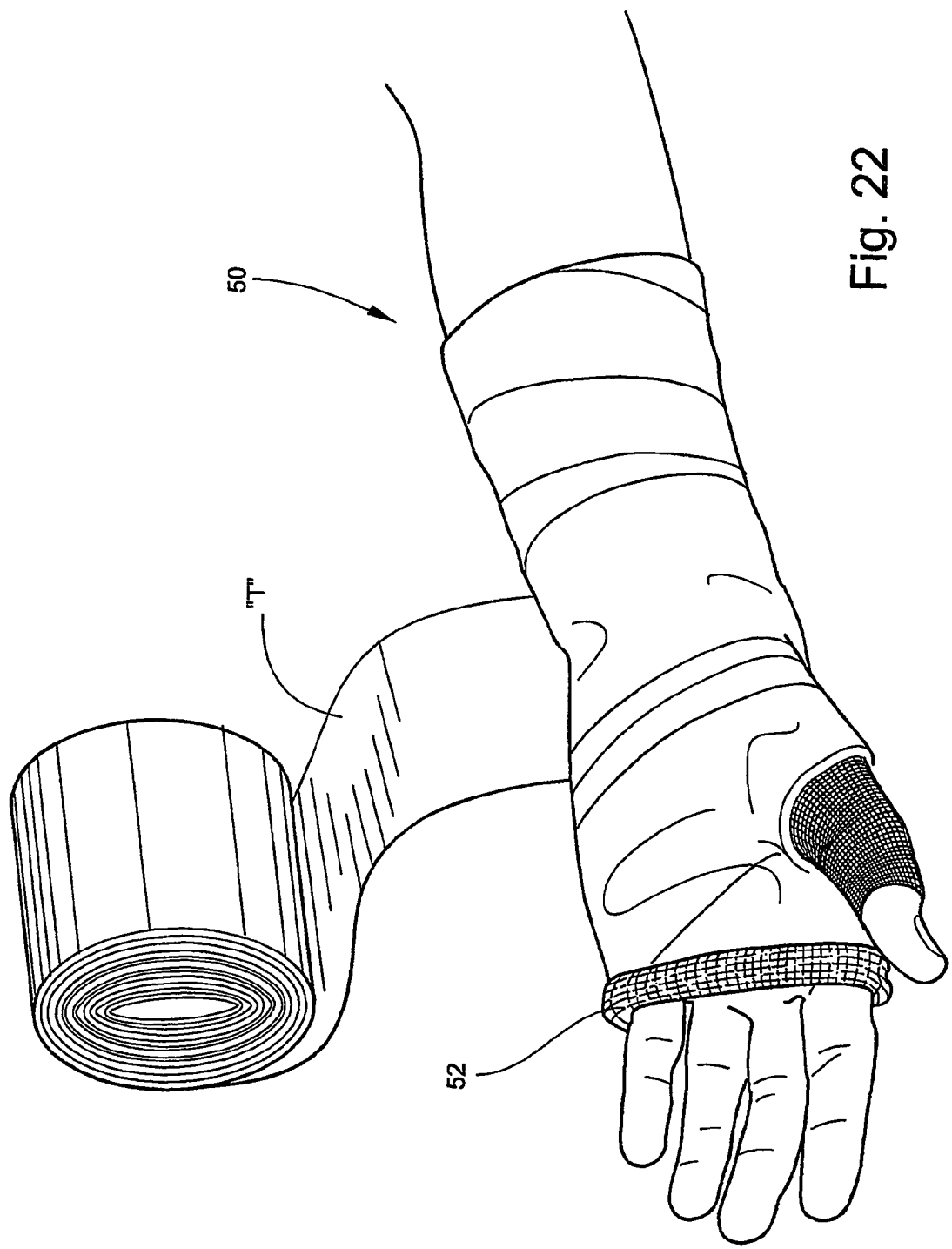

A cast liner according to another embodiment of the present invention is illustrated in FIG. 14 and shown generally at reference numeral 40. The cast liner 40 is shown, as intended for use, in tubular form. The tube may be formed by knitting a sliver on a conventional circular knitting machine, or knitting on a flat-bed machine, and then forming the flat fabric into a tube using a seam, such as an overedge or serging seam. The knitting machine may have a double-knit capability.

The cast liner 40 is knitted from spun synthetic fiber yarns, such as conventional microfiber acrylic, polypropylene or polyester yarns. The water-resistant nature of the cast liner 40 results from a process of coating the knitted fabric with a silicone or polyurethane-based monomer. The cast liner 40 may be formed from filament or spun yarns, with spun textured yarns being the preferred construction.

In general, the outer surface 41 of the cast liner 40 has a soft, "popcorn" appearance and feel resulting from the use of yarns or slivers formed from microfiber synthetic yarns, as is shown in FIG. 15, knitted under low tension with sufficient overfeed to allow the yarns to loop upwardly and form the "popcorn"-like puffs. The surfaces 41 and 42 show a distinct, puffy, "popcorn" appearance caused by adjacent ranks and files of microfiber yarns contracted by the elastic yarns. Except for actual yarn construction and appearance, characteristics of the cast liner 40 are similar to the cast liner 10, and is also suitable for use as a cushion layer for a splint product.

Referring now to FIGS. 16-22, a medical bandaging product in the form of a cast liner 50 according to the preferred embodiment of the invention is shown. The cast liner 50 is shown, as intended for use, in tubular form. The tube may be formed by knitting yarns or slivers on a conventional circular knitting machine, or knitting on a flat-bed machine, and then forming the flat fabric into a tube using a seam, such as an overedge or serging seam. The knitting machine may have a double-knit capability.

The cast liner 50 is knitted from spun synthetic fiber yarns, such as conventional microfiber acrylic, polypropylene or polyester yarns. The water-resistant nature of the cast liner 50 results from a process of coating the knitted fabric with a silicone or polyurethane-based monomer. The cast liner 50 may be formed from filament or spun yarns, with spun textured yarns being the preferred construction.

The cast liner 50 has a soft, conformable construction with outer and inner surfaces 51 and 52 characterized by a radially-extending ribs 54, i.e., a rib 54 that extends spirally around the periphery of the cast liner 50, rather than longitudinally along the cast liner, as with cast liner 10. The ribs 54 thus provide close and regularly spaced-apart weakness areas between adjacent ribs 54 that allow the cast liner 50 to be conformed around the bend of, for example, the elbow or foot, with a minimum of creasing. Rather, the cast liner 50 will bend naturally and progressively at points between adjacent ribs 54 around and along the area where the bend is most pronounced. Accommodating the natural direction of bending in this manner greatly increases comfort and reduces or eliminates the creation of pressure points that can cause chafing, pressure sores and, in extreme cases, infection.

In FIGS. 18-22 the cast liner 50 is shown being applied to a limb and wrapped with a conventional cast tape "T".

| A preferred embodiment of the cast liner 50 is as follows: | |
|---|---|
| Yarn | Enya Neofil 2/100 Decitex 80 filament white textured polypropylene, or |
| | Enya Neofil 2/70 Decitex 80 filament white texture polypropylene |
| | Dorlastan 70 denier elastane Polyester/Polyurethane |
| Construction | 18.3 ribs/inch (7.2 ribs/cm), 8 needles per rib |
| | 5 inch diameter cylinder, 440 needles |
| | 4 ends of 1/100/80 Enya polypropylene |
| | 2 ends of 70 denier Dorlastan polyester/polyurethane |
| | 4 feeds |
| |     1 feed--2/100/80 polypropylene |
| |     2 feed--2/100/80 + 70 Denier Dorlastan |
| |     3 feed--2/100/80 polypropylene |
| |     4 feed--2/100/80 + 70 Denier Dorlastan |
| Thickness | 2/5-40 mm |
| Courses | 30-60 inch |

Dorlastan polyester/polyurethane is a dry spun elastic filament that provides durability, long-term dimensional stability and soft elasticity, and is manufactured by Bayer Faser GmbH.

Figure 23:
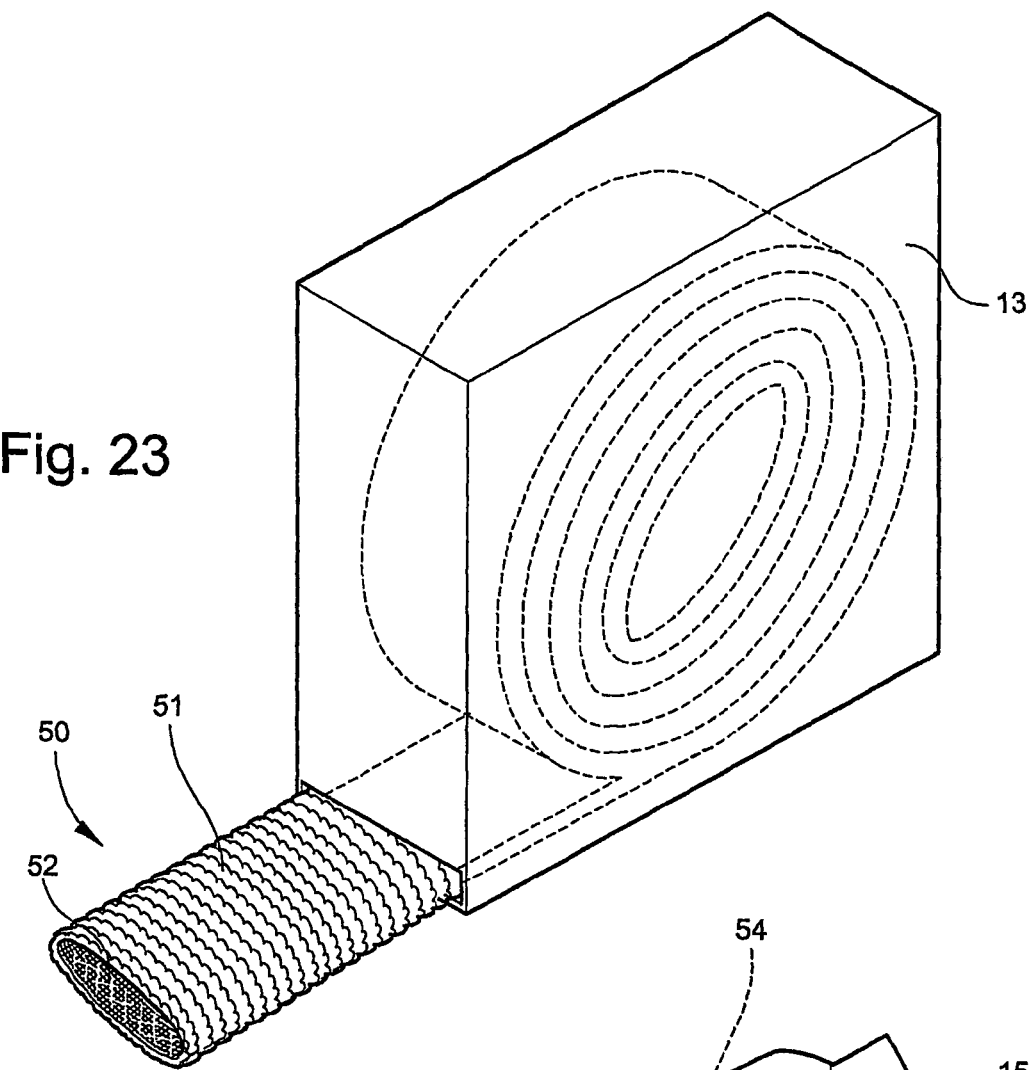
FIG. 23 shows a continuous length of the cast liner in a dispensing package.

Referring to FIG. 23, a continuous length, for example 10-15 meters, of the cast liner 50 is shown formed into a coil and packaged in a dispensing box 13. A desired length is obtained by extracting the free end of the cast liner 50 from the dispensing box 13 and cutting off the desired length.

Figure 24:
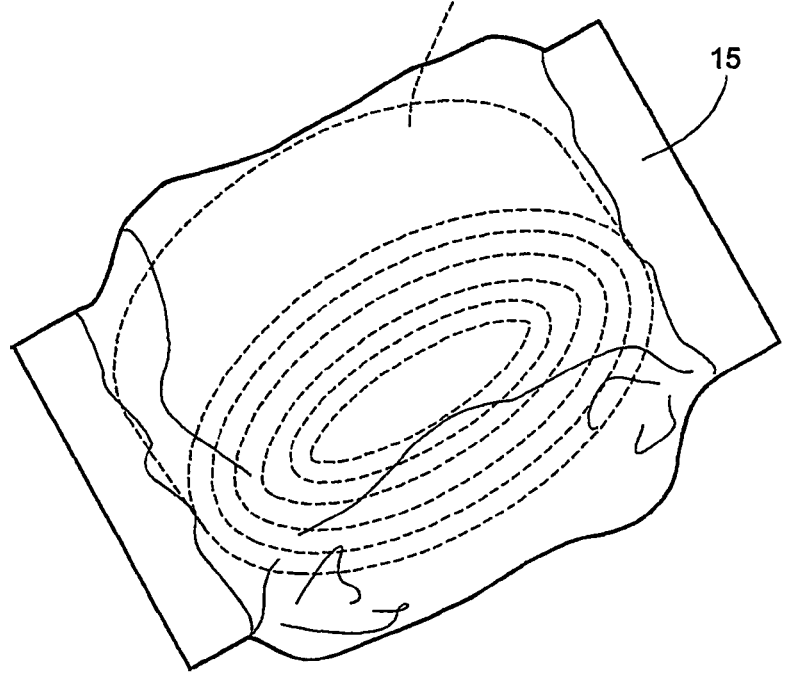
FIG. 24 shows a pre-cut length of the cast liner packaged for distribution and storage until ready for use.
Figure 25:
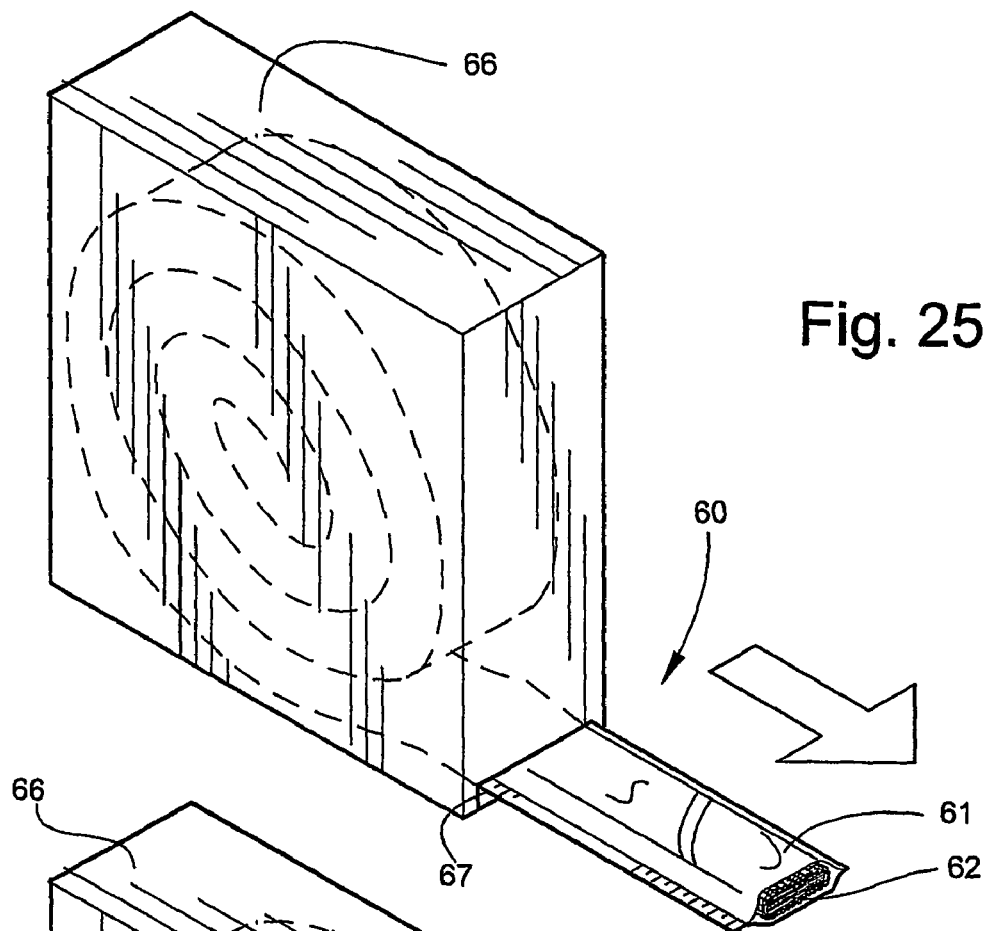
FIG. 25 shows a continuous length of the medical bandaging product in the form of a synthetic splint being dispensed from a dispensing carton.
Figure 26:
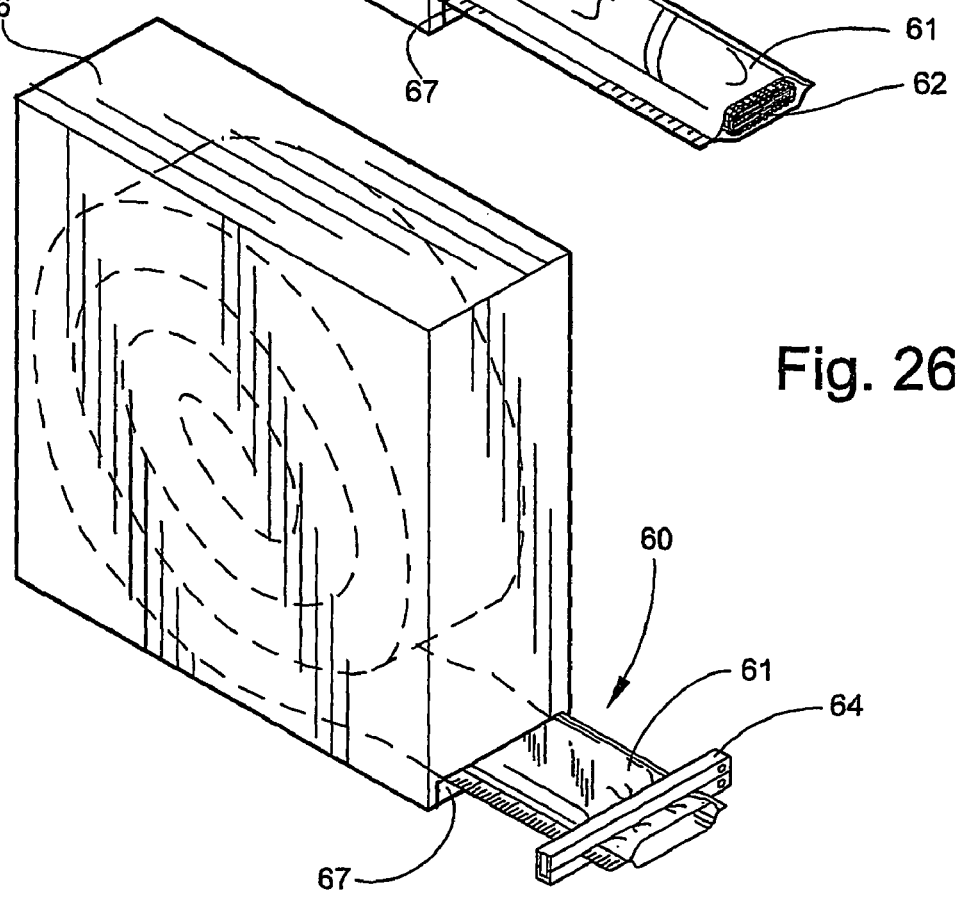
FIG. 26 shows the continuous length of medical bandaging product sealed to prevent moisture intrusion.
Figure 27:
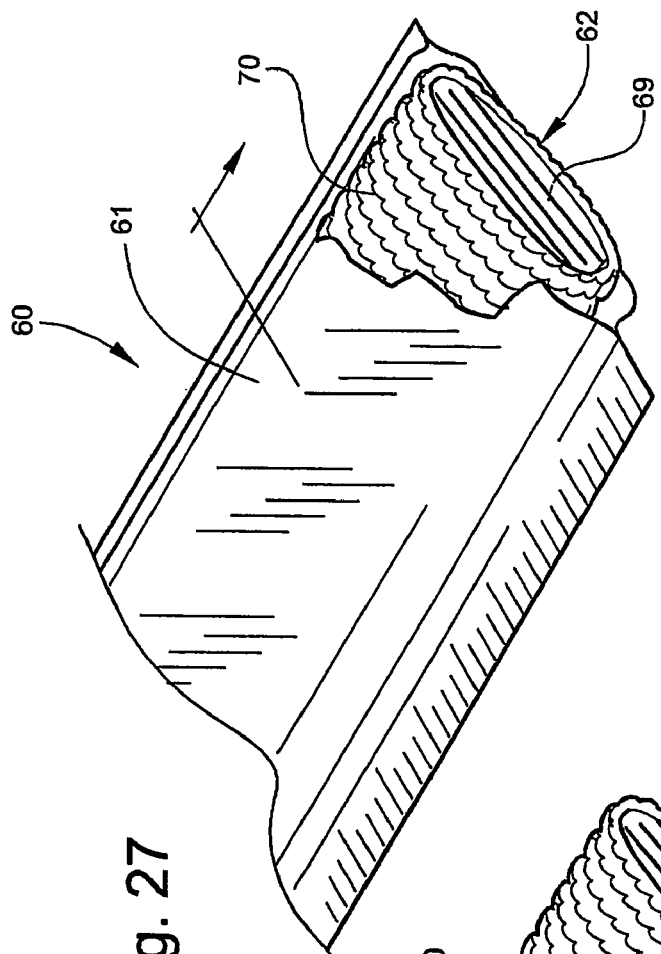
FIG. 27 is a partial perspective view with parts broken away of a synthetic splint product utilizing the medical bandaging product as a protective cushion between the patient and the substrate.
Figure 28:
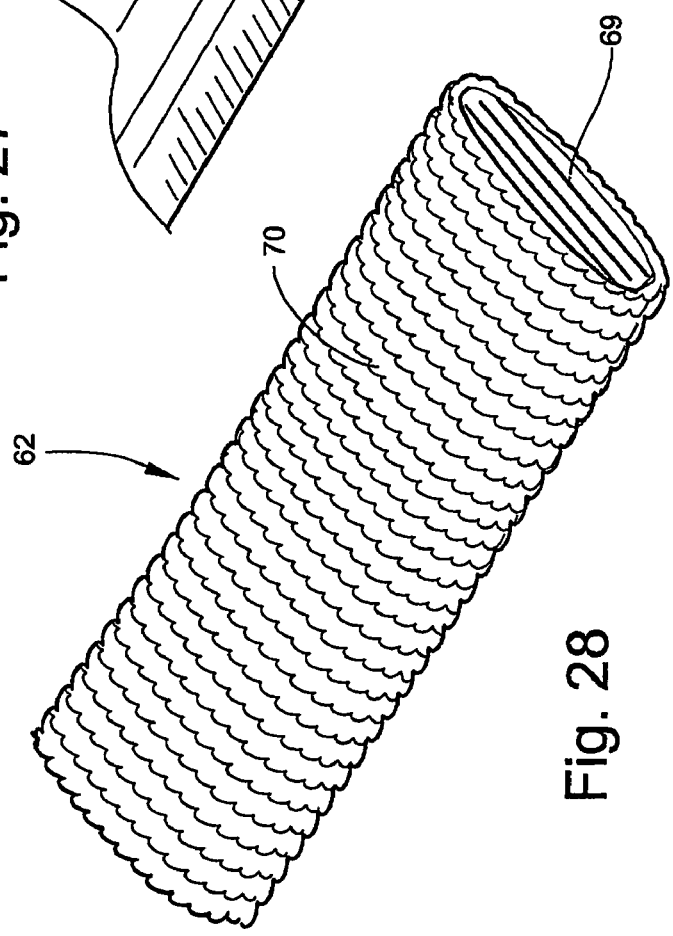
FIG. 28 is a perspective view of a cut length of the synthetic splint product removed from the foil protective sleeve.
Figure 29:
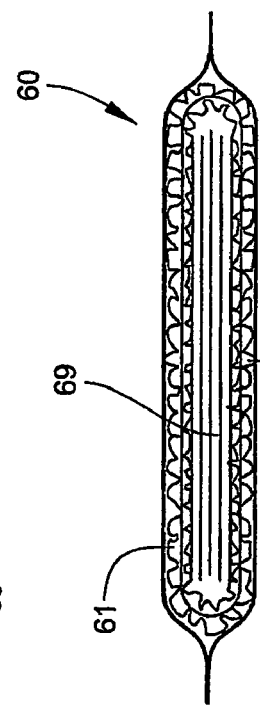
FIG. 29 is a cross-section of the synthetic splint product shown in FIG. 10.

A pre-cut length 54 of the cast liner 40 is shown in FIG. 24, packaged in rolled form in a protective package 15. The pre-cut length 54 of the cast liner 40 is formed by cutting a longer length of the cast liner 50 into the desired lengths, and then packaging them in a suitable fashion for subsequent use.

Referring now to FIGS. 25-29, the same material used as the cast liner 50 can be used as a padding layer for a medical bandaging product of the type that incorporates a moisture curable resin into a substrate for use as a splint.

The medical bandaging product 60 is comprised generally of an outer elongate sleeve 61 which is formed of a moisture-impervious material such as a laminated plastic/foil sheet material. Sleeve 61 is heat sealed along opposite, parallel extending sides to form an elongate tube. An elongate splint material 62, described in detail below, is positioned within sleeve 61 and is maintained in substantially moisture-free conditions until dispensed. The end of sleeve 61 is sealed with sealing means, such as a clip 54, shown in FIG. 26, to prevent hardening of the unused portion of the splint material 62. The elongate sleeve 61 is rolled, festooned or otherwise configured to fit within a dispensing carton 66, and is dispensed through a slot 67.

Once the appropriate length of the splint material 62 has been dispensed and cut from the roll, it is removed from sleeve 61 and the cut portion of the sleeve 61 is discarded.

Splint material 62 is formed of a substrate 69 comprised of a suitable number, for example, 6, of overlaid layers of a woven or knitted relatively open fabric, constructed of, for example, fiberglass, or various combinations of synthetic fibers. Substrate 69 is contained within a tubular length of a padding layer 70 having a construction as identified with relation to the cast liner 50. The padding layer 70 provides a cushioning protective layer between the skin of the patient and substrate 69. Substrate 69 is impregnated or coated with a reactive system which remains stable when maintained in substantially moisture-free conditions but which hardens upon exposure to sufficient moisture to form a rigid, self-supporting structure. A typical formulation of the reaction system is as set forth in the table above with reference to the splint material 22.

Hardening of the substrate 69 and thus of the splint material 62 is activated by dipping or spraying with water. Then excess moisture is squeezed from the splint material 62 with a towel.

Figure 30:
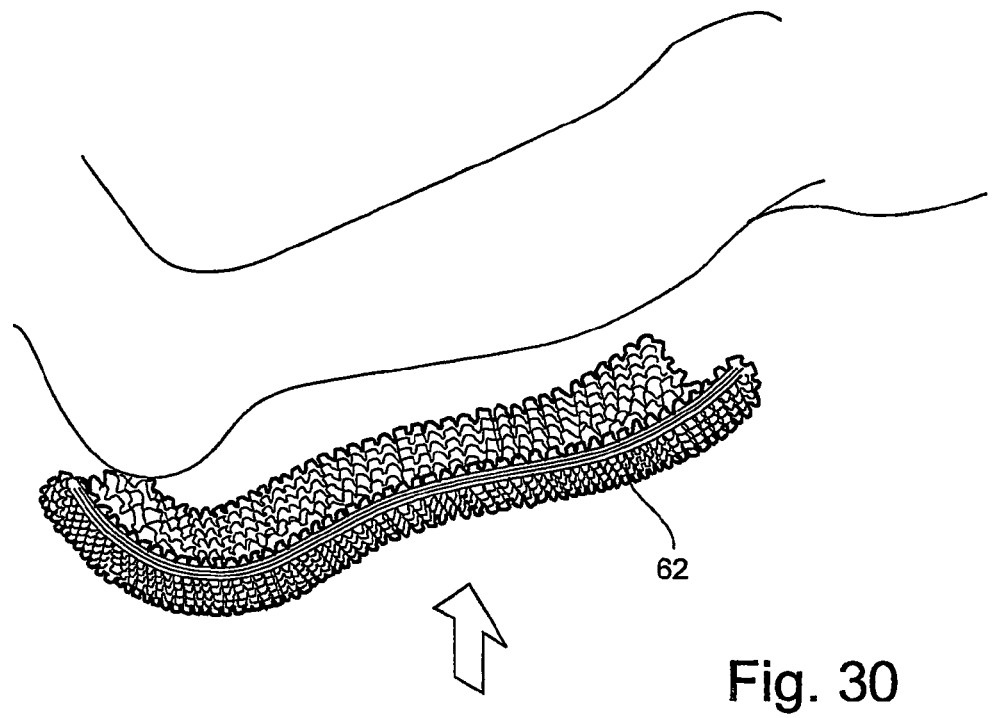
FIGS. 30 and 31 show application of a length of the synthetic splint product to a limb.
Figure 31:
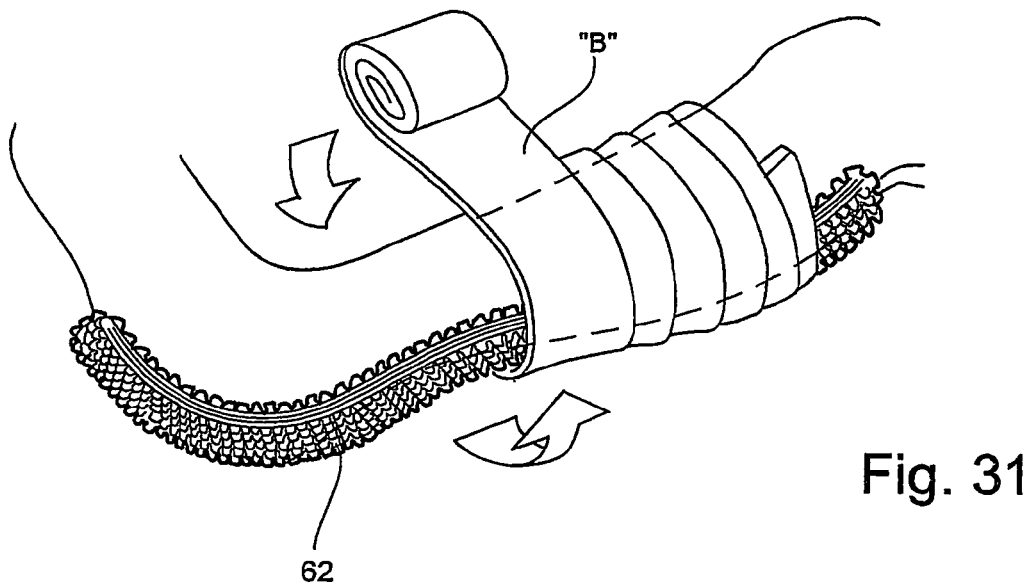

In FIG. 30, an appropriate length of splint material 62 is formed to the shape of the body member to be immobilized as described above with reference to a posterior short leg splint, and overwrapped with a conventional elastic bandage "B", as is shown in FIG. 31.

A medical bandaging product is described above. Various details of the invention may be changed without departing from its scope. Furthermore, the foregoing description of the preferred embodiments of the invention and the best mode for practicing the invention are provided for the purpose of illustration only and not for the purpose of limitation-the invention being defined by the claims.

We claim:
1. A splint product in roll form for being dispensed in predetermined lengths suitable for a given medical use, comprising:
 (a) an elongate sleeve formed of moisture-impervious material and sealable to prevent entry of moisture;
 (b) an elongate medical material positioned in said sleeve and sealed therein against entry of moisture until use, said medical material comprising:
  (i) a substrate;
  (ii) a reactive system impregnated into or coated onto said substrate, said system remaining stable when maintained in substantially moisture-free conditions and hardening upon exposure to sufficient moisture to form a rigid, self supporting structure; and
  (iii) a soft, flexible, protective tubular wrapping enclosing said substrate along its length to provide a cushioning barrier between the substrate and the skin of a patient when the material is in use, said soft, flexible protective wrapping comprising a rib-knitted fabric constructed of synthetic yarns selected from the group consisting of acrylic, polyester and polypropylene yarns, said tubular wrapping comprising an inner surface having longitudinally extending ribs arranged around the inner surface and extending along the length thereof and that separate when applied to channel air flow and remove moisture from the skin between the ribs, and an outer surface having a plush texture; and
 (c) means for resealing said sleeve against entry of moisture after a predetermined length of said bandaging product has been dispensed for use to prevent hardening of said substrate remaining in said sleeve.

2. A splint product according to claim 1, wherein said rib-knitted fabric of the protective wrapping is circular-knitted to define a tube, with the ribs extending longitudinally along the length of the tube.

3. A splint product according to claim 1, wherein said rib-knitted fabric of the protective wrapping is circular-knitted to define a tube, with the ribs extending radially around the periphery of the tube.

4. A splint product according to claim 3, and including an elastic yarn incorporated into the fabric to provide elasticity to the fabric.

5. A splint product in roll form for being dispensed in predetermined lengths suitable for a given medical use, comprising:
 (a) an elongate sleeve formed of moisture-impervious material and sealable to prevent entry of moisture;
 (b) an elongate medical material positioned in said sleeve and sealed therein against entry of moisture until use, said medical material comprising:
  (i) a substrate;
  (ii) a reactive system impregnated into or coated onto said substrate, said system remaining stable when maintained in substantially moisture-free conditions and hardening upon exposure to sufficient moisture to form a rigid, self supporting structure; and
  (iii) medical bandaging product comprising a soft, flexible protective wrapping enclosing said substrate along its length to provide a cushioning barrier between the substrate and the skin of a patient when the material is in use, said soft, flexible protective wrapping comprising a rib-knitted fabric constructed of synthetic yarns selected from the group consisting of acrylic, polyester and polypropylene yarns, said wrapping comprising an inner surface having longitudinally extending ribs arranged around the inner surface and extending along the length thereof and that separate when applied to channel air flow and remove moisture from the skin between the ribs, and an outer surface having a plush texture; and (c) means for resealing said sleeve against entry of moisture after a predetermined length of said bandaging product has been dispensed for use to prevent hardening of said substrate remaining in said sleeve.

6. A splint product according to claim 5, wherein said rib-knitted fabric of the protective wrapping is circular-knitted to define a tube, with the ribs extending longitudinally along the length of the tube.

7. A splint product according to claim 5, wherein said rib-knitted fabric of the protective wrapping is circular-knitted to define a tube, with the ribs extending radially around the periphery of the tube.

8. A medical bandaging product, comprising a rib-knitted fabric constructed of synthetic yarns selected from the group consisting of acrylic, polyester and polypropylene yarns, said fabric knitted into a tube for positioning over a limb and including an inner surface having longitudinally extending ribs arranged around the inner surface and extending along the length thereof and that separate when applied to the limb to channel air flow and remove moisture from the skin between the ribs, and an outer surface having a plush texture; and an effective amount of a water-repelling treatment applied to the fabric for imparting water-repellent characteristics to the fabric.

9. A medical bandaging product according to claim 8, wherein said rib-knitted fabric is circular-knitted to define the tube, with the ribs extending radially around the periphery of the tube.

10. A medical bandaging product according to claim 8, and including an elastic yarn incorporated into the fabric to provide elasticity to the fabric.

11. A medical bandaging product, comprising a knitted fabric constructed of synthetic yarns selected from the group consisting of acrylic, polyester and polypropylene yarns, said fabric knitted into a tube for positioning over a limb and including an inner surface having longitudinally extending ribs arranged around the inner surface and extending along the length thereof and that expand when applied to the limb to channel air flow and remove moisture from the skin between the ribs; said fabric further having a knit structure wherein a major surface of the fabric comprises regular courses and wales of soft, deformable tufts defined by yarn loops extending outwardly above a base of the fabric.

12. A medical bandaging product according to claim 11, and including an elastic yarn incorporated into the fabric to provide elasticity to the fabric.

13. A medical bandaging product according to claim 11, and including an effective amount of a water-repelling treatment applied to the fabric for imparting water-repellent characteristics to the fabric.

* * * * *